United States Patent [19]

Sutter et al.

[11] Patent Number: 5,169,951

[45] Date of Patent: Dec. 8, 1992

[54] PROCESS FOR PREPARING NEMATICIDAL COMPOSITIONS

[75] Inventors: Marius Sutter, Basel; Walter Kunz, Oberwil, both of Switzerland

[73] Assignee: Ciba-Geigy Corporation, Ardsley, N.Y.

[21] Appl. No.: 684,549

[22] Filed: Apr. 11, 1991

[30] Foreign Application Priority Data

Apr. 23, 1990 [CH] Switzerland ............... 1358/90
Jan. 28, 1991 [CH] Switzerland ............... 256/91

[51] Int. Cl.$^5$ .......................................... C07D 275/04
[52] U.S. Cl. ................................. 548/212; 548/207; 548/209
[58] Field of Search .................. 548/207, 212, 209

[56] References Cited

U.S. PATENT DOCUMENTS 3,707,364 12/1972 Becke et al. ............... 71/90
4,694,014 9/1987 Beriger ..................... 514/363
4,910,210 3/1990 Beriger et al. .............. 514/363

FOREIGN PATENT DOCUMENTS 3018108 11/1981 Fed. Rep. of Germany.
2002891 10/1969 France.

OTHER PUBLICATIONS

J. Markert et al., *Liebigs Ann Chem.*, "Darstellung von 1,2-Benziothiazolen und einige Folgereaktionen," pp. 768–778 (1980).

L. Fiesa et al., "Reagents of Organic Synthesis," vol. 1, pp. 481–484, John Wiley and Sons, New York (1967).

A. Ricci et al. (I), *Annali de Chimica*, "Nuovesintesi del Genzoisothiazolo," 53, pp. 577–587 (1963).

A. Ricci et al. (II), *Annali de Chimica*, "Ricerche sul Genzoisotiazolo," 53 pp. 1860–1868 (1963).

A. Ricci et al. (III) *Chemical Abstracts* 60: 1206b (1964) abstract of Ann. Chim. (Rome) 53 (12) 1860–1868 (1963).

J. March, "Advanced Organic Chemistry," 3rd ed, pp. 360-362, and 915, John Wiley and Sons, New York (1985).

Chemical Abstracts 60:12000d (1964).

*Primary Examiner*—Richard L. Raymond
*Assistant Examiner*—Mark W. Russell
*Attorney, Agent, or Firm*—Marla J. Mathias; Edward McC. Roberts

[57] ABSTRACT

Nematicidal compositions which comprise as active ingredient compounds of formula I

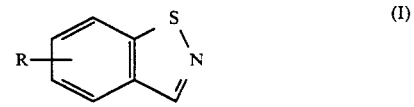

(I)

wherein R is nitro or halogen, and also processes for the preparation of the compounds of formula I, novel intermediates of the preparation process and methods of using the compounds and the compositions in the control of nematodes are described.

6 Claims, No Drawings

PROCESS FOR PREPARING NEMATICIDAL COMPOSITIONS

The present invention relates to novel nematicidal compositions that comprise at least one benzisothiazole as active ingredient, and to their use for controlling nematodes, especially plant-destructive nematodes.

The invention relates also to novel nematically active benzisothiazoles and to processes for the preparation thereof.

The nematicidally active benzisothiazoles according to the present invention have the general formula I

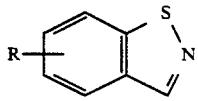
(I)

wherein R is nitro or halogen.

Halogen here and in the following description may be fluorine, chlorine, bromine or iodine.

The known nematically active compounds have hitherto been unable fully to meet the requirements made of them in practice.

The object of the present invention was, therefore, to provide novel nematicidal compositions having advantageous properties.

With the provision of the compositions according to the invention comprising the compounds of formula I as active ingredient and, in addition, at least one carrier, it is now possible to make a valuable contribution to controlling plant nematodes which cause considerable agricultural damage to plants. In this manner, losses in yield of cultivated plants, for example potatoes, cereals, beet crops, rape, cabbage, tobacco, soybeans, cotton, maize, rice and vegetables, and also damage caused in tree nurseries and to ornamentals can be inhibited over a prolonged period. The compositions according to the invention are distinguished especially by the fact that they effectively control soil nematodes that parasitise roots, for example nematodes of the genera Heterodera and Globodera (cystogenic nematodes), Meloidogyne (root-knot nematodes) and also of the genera Radopholus, Pratylenchus, Tylenchulus, Longidorus, Trichodorus and Xiphinema. The nematode genera Ditylenchus (stem parasites), Aphelenchoides (leaf nematodes) and Anguina (blossom nematodes) can also be effectively controlled with the compositions according to the invention.

The compositions comprising the compounds of formula I as active ingredient are used especially for the successful control of particularly harmful nematode species of the genus Meloidogyne, for example *Meloidogyne incognita*, and of the genus Heterodera, for example *Heterodera glycines* (soybean cyst nematode).

To control plant nematodes and for the preservation of plant health, the novel compounds may be used curatively, preventively or systemically. They have a broad spectrum of activity against the various nematode species and therefore meet the requirements made of them in practice. The nematicidal mode of action of the compositions according to the invention is coupled in advantageous manner with a relatively low phytotoxicity. In comparison with known nematicidal compositions, the compositions according to the invention exhibit only low toxicity to humans.

Nematicidal activity is ascertained and also determined by inhibition of root-knot formation on a treated cultivated plant in comparison with an untreated plant.

The activity is designated "good" when attack on the treated plant is less than 20% of the attack on the untreated plant.

Of the compounds of formula I, preference is given as nematicides to those of formula I'

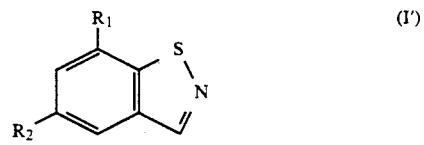
(I')

wherein $R_1$ is hydrogen or halogen, and $R_2$ is nitro when $R_1$ is hydrogen and is hydrogen when $R_1$ is halogen.

Of the compounds of formula I, those of formula I''

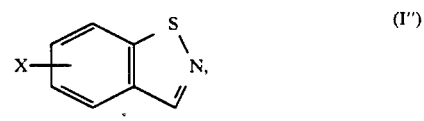
(I'')

wherein X is bromine, fluorine or iodine, exhibit remarkable nematicidal activity.

These compounds are novel, and the present invention relates also to them. Of the last-mentioned compounds, prominence is to be given to those of formulae Ia, Ic, Id and Ie

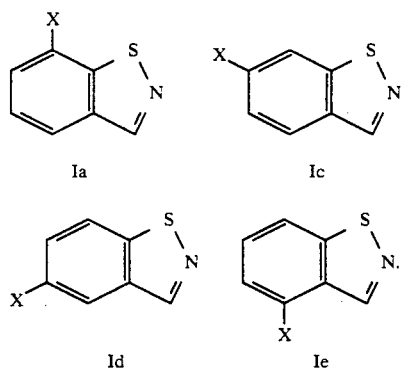

Of the compounds of formula I, preference is given on account of their nematicidal activity also to 5-nitrobenzisothiazole and 7-chlorobenzisothiazole.

5-Nitrobenzisothiazole and a process for the preparation thereof are described in DE-OS 3,018,108. In that publication it is disclosed that the compounds of formula

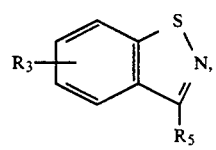

wherein $R_3$ is hydrogen, an aliphatic, cycloaliphatic or optionally annellated aromatic radical, halogen, an alkoxy group, a nitro group or the radical

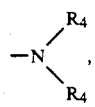

in which $R_4$ is in each case hydrogen or an aliphatic, cycloaliphatic, araliphatic or aromatic radical, and $R_5$ is hydrogen or an aromatic or heterocyclic radical, are valuable intermediates for the manufacture of dyes, pharmaceuticals, etc.

7-Nitrobenzisothiazole is known from the literature [J. Chem. Soc. Perkin Trans. I, 385 (1984)]. It is formed in addition to 4- and 5-nitrobenzisothiazole in the nitration of benzisothiazole with potassium nitrate in concentrated sulfuric acid.

In patent specification CH 539385 it is mentioned that benzisothiazoles substituted in the 3-position have herbicidal activity.

Publication FR 2,002,891 describes benzisothiazoles of formula

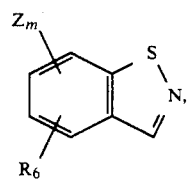

wherein Z is nitro or halogen, m is a number 1 or 2 and $R_6$ is hydrogen or alkyl, which are suitable for the control of insects and acarids. No mention is made of nitrobenzisothiazoles.

Four monochlorobenzisothiazoles are known; 4-chlorobenzisothiazole from Liebigs Ann. Chim. 768 (1980) and ibid 729, 146 (1969), 5-chlorobenzisothiazole from DE-OS 3,018,108 and 6-chlorobenzisothiazole from Ann. Chim. (Rome) 53,577 (1963); 7-chlorobenzisothiazole is described in Ann. Chim. (Rome) 53 (12) 1860–1868 (1963), CA 60, 12000d. The compound was prepared starting from 7-aminobenzisothiazole via the diazonium chloride by a Sandmeyer reaction, in the presence of Cu(I)Cl.

While thiadiazoles having nematicidal activity are known from EP-0 321408 and EP-0 217747, there is no mention in the literature of isothiazoles or benzisothiazoles having that property.

The novel compounds of formula I″ can be prepared by diazotising an aminobenzisothiazole of formula II to form the diazonium salt of formula III and reacting the latter, optionally in the presence of Cu(I)X or Fe(II)X$_2$, with the corresponding hydrohalic acid of the formula HX,

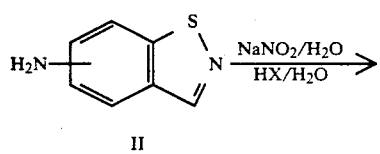

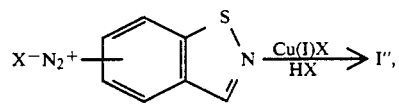

wherein X is bromine, fluorine or iodine.

Prominence is to be given to the preparation of the novel compounds of formula Ia from 7-aminobenzisothiazole in accordance with this process.

In the case of fluorine substitution (X=F), the reaction proceeds smoothly in anhydrous hydrofluoric acid. Another possible method of preparing the fluorine compounds of formula Ia (X=F) is the thermal decomposition of the diazonium tetrafluoroborate of formula III (X$^-$=BF$_4$$^-$), which can readily be isolated. This procedure is described in Houben-Weyl's "Die Methoden der Organischen Chemie", Vol. 5/3, pp. 213 ff. (1962) in which analogous reaction sequences are used as an example.

In the case of iodine substitution (X=I), the Cu(I)I can be replaced by KI.

The diazotisation of the aromatic amine of formula II is effected in accordance with known methods, preferably with alkali metal nitrite and hydrohalic acid in a cold aqueous solution. The conversion of the diazonium salt into the halogen compound of formula Ia is carried out in accordance with the known principles of the Sandmeyer reaction, see Houben-Weyl, "Die Methoden der Organischen Chemie", Vol. 5/4, pp. 437 ff., 639 ff. (1960); ibidem, Vol. 5/3, p. 213, (1962).

The compounds of formula I

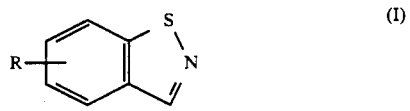

can be prepared in accordance with a novel process by reacting a substituted halobenzaldehyde of formula V with a thioalcohol R$_9$SH in solution, in the presence of a base, to form the thioether of formula VI, which is then reacted, with or without isolation, with hydroxylamine-O-sulfonic acid in solution and cyclised to form the desired product,

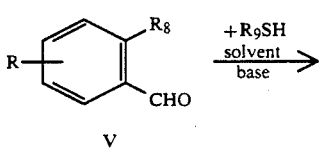

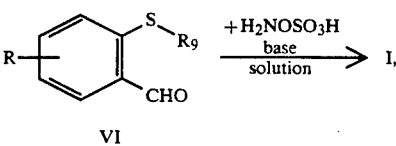

wherein R is nitro or halogen, R$_8$ is halogen and R$_9$ is C$_1$–C$_{30}$alkyl, C$_3$–C$_7$cycloalkyl or C$_7$–C$_9$aralkyl.

According to a preferred form the thioether of formula VI is reacted with hydroxylamine-O-sulfonic acid in solution and cyclised by the addition of a base to form the desired product.

Alkyl here and in the following description shall be understood as meaning straight-chain and branched-chain groups, for example ethyl, propyl, butyl, isobutyl or tert-butyl.

Of the mercaptans, $C_1$–$C_4$alkylmercaptans or benzylmercaptan are preferred.

The reaction can be preferably carried out in the presence of metal salts, for example, copper, nickel or palladium salts.

Suitable bases for the first stage of this reaction sequence are, for example, hydrides, amides, alcoholates, carbonates or hydrogen carbonates of alkali metals or alkaline earth metals, preferably potassium carbonate or sodium carbonate. Advantageously, the reaction is carried out in alcohols or in aprotic solvents, for example dimethylformamide, dimethyl sulfoxide, dimethylpropyleneurea or dimethylethyleneurea, or in ethers, such as diethyl ether or tetrahydrofuran, at from 0° to 70° C., preferably at room temperature.

Suitable bases for the second stage are alkali metal carbonates or hydrogen carbonates, for example sodium hydrogen carbonate. Tertiary amines, for example triethylamine or pyridine, may also be mentioned as suitable bases for the second stage.

This process is novel, and the invention relates also thereto. The intermediates of formula VI wherein R is halogen or nitro and $R_9$ is $C_1$–$C_{30}$alkyl, $C_3$–$C_7$cycloalkyl or $C_7$–$C_9$aralkyl, with the exception of 2-methylthio-5-chlorobenzaldehyde and 2-benzylthio-6-chlorobenzaldehyde, are also novel, and the present invention relates also to them.

Of the compounds of formula VI, prominence is to be given as intermediates to those compounds wherein $R_9$ is $C_1$–$C_6$alkyl or a benzyl radical. Of that group, preference is given to those compounds wherein $R_8$ is chlorine. Of those intermediates, 2-benzylthio-3-chlorobenzaldehyde is especially preferred.

The starting materials for the mentioned preparation processes are either known, commercially available compounds or they can be prepared in accordance with known processes.

Suitable solvents for the second stage are aprotic organic solvents, for example methylene chloride, ethers, for example diethyl ether, dioxane or tetrahydrofuran, esters, for example ethyl acetate, hydrocarbons, for example hexane, cyclohexane, methylcyclohexane or toluene, and mixtures thereof with water. The reaction temperature in the second stage is from −20° to 100° C., preferably from 20° to 50° C.

Of these novel processes, according to the present invention prominence is to be given to the process for the preparation of compounds of formula Ib

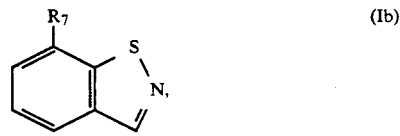

which comprises reacting a 2,3-dihalobenzaldehyde of formula VII with benzylmercatane in solution, in the presence of a base, to form the thioether of formula VIII, which is then cyclised, with or without isolation, with hydroxylamine-O-sulfonic acid in solution, to form the desired product,

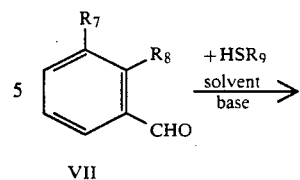

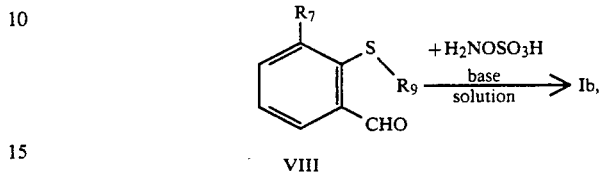

wherein $R_7$ and $R_8$ are identical or different halogens and $R_9$ is the benzyl radial.

According to a preferred form of this process the thioether of formula VIII is reacted with hydroxylamine-O-sulfonic acid in solution and cyclised by the addition of a base to form the desired product.

According to a specially preferred form, the intermediate of formula VIII is reacted with hydroxylamine-O-sulfonic acid at pH=5 and the cyclisation is effected by the subsequent addition of a base.

The process is preferred when $R_7$ and $R_8$ are chlorine.

In addition, the present invention also includes the preparation of nematicidal compositions, which comprises homogeneously mixing compounds of formula I with one or more of the carriers and adjuvants described herein. The compositions according to the invention accordingly comprise an effective amount of at least one of the compounds of formula I.

The invention also includes a method of treating plants, which comprises applying thereto the compounds of formula I or the novel compositions.

A preferred method of applying a compound of formula I or a nematicidal composition comprising at least one of those compounds is incorporation into the soil, which comprises treating the locus of the plants with a liquid or solid formulation.

The compounds of formula I can, however, also be applied to the seeds (dressing/coating) either by impregnating the seeds with a liquid formulation of the active ingredient or by coating them with a solid formulation. In special cases, other methods of application are also possible, for example selective treatment of the plant stems, buds or leaves.

The compounds of formula I are normally applied in the form of formulated compositions and can be applied to the area or plant to be treated, simultaneously or in succession, with further compounds. These further compounds can also be other compositions which are used in agriculture and serve to increase production by promoting the growth of useful plants, such as fertilisers, herbicides, insecticides, fungicides, molluscicides, etc., or mixtures of several of these preparations, if desired together with further carriers, surfactants or other application-promoting adjuvants customarily employed in formulation technology.

Suitable carriers and adjuvants can be solid or liquid and correspond to the substances ordinarily employed in formulation technology, e.g, natural or regenerated mineral substances, solvents, dispersants, wetting agents, tackifiers, thickeners, binders or fertilisers.

The compounds of formula I are used in unmodified form or, preferably, together with the adjuvants conventionally employed in formulation technology. They are formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, dusting, scattering or pouring, are chosen in accordance with the intended objectives and the prevailing circumstances. Advantageous rates of application are normally from 0.1 to 10 kg of active ingredient (a.i.) per hectare; preferably from 0.3 to 5 kg a.i./ha.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyllaurin salts and modified and unmodified phospholipids.

More frequently, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The novel surfactants customarily employed in formulation technology are described inter alia in the following publications:

"McCutcheon's Detergents and Emulsifiers Annual", MC Publishing Corp., Ridgewood, N. J., 1979; Dr. Helmut Stache "Tensid Taschenbuch", Carl Hanser Verlag, Munich/Vienna.

The agrochemical compositions comprise an effective amount, i.e. usually 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

The present invention relates also to such agrochemical compositions.

The following Examples illustrate the invention in greater detail, but do not limit the invention.

P. PREPARATION EXAMPLES

P.1 65 ml of benzylmercaptan are added to a suspension comprising 500 ml of dimethylformamide, 100 g of 2,3-dichlorobenzaldehyde and 100 g of potassium carbonate, and the mixture is stirred overnight at 20°-40° C. The reaction mixture is then diluted with water and diethyl ether and stirred. After separation of the layers, the ethereal solution is washed with saturated sodium chloride solution, the ether is evaporated off, and the residue is recrystallised from ethanol. The resulting 2-benzylthio-3-chlorobenzaldehyde melts at 73°-74° C.; the yield is 118 g (90% of the theoretical yield).

101 g of 2-benzylthio-3-chlorobenzaldehyde, 47 g of hydroxylamine-O-sulfonic acid and 6 g of sodium sulfate are stirred in 200 ml of water for one hour. After the addition of a further 100 ml of water and 100 ml of methylene chloride, 120 g of sodium hydrogen carbonate are added gradually, with uniform evolution of gas. After a further 1½ hours, the mixture is extracted with methylene chloride, the organic layer is washed with brine, and the solvent is evaporated off in vacuo.

The residue is dissolved in hexane/ethyl acetate=95:5 and the solution is chromatographed over silica gel.

Evaporation of the solvent yields 62.8 g of 7-chlorobenzisothiazole, comp. no. 2 (Table). Melting point: 50°-51° C.

P.2 4-Nitrobenzisothiazole, 5-nitrobenzisothiazole and 7-nitrobenzisothiazole 300 g of benzisothiazole are added, with cooling, to 750 ml of concentrated sulfuric acid, the solution is cooled to −40° C., and 227.5 g of potassium nitrate are added in portions, in such a manner that the temperature does not rise above room temperature. After standing at room temperature for 15 hours, the reaction mixture is poured onto ice and the solid portion is filtered off and dried. The product is chromatographed on silica gel with tetrahydrofuran:methylene chloride:hexane 5:10:85. After evaporation, there are isolated from the fractions 5.5% of the theoretical yield of 4-nitrobenzisothiazole, 56.5% of the theoretical yield of 5-nitrobenzisothiazole and 36.8% of the theoretical yield of 7-nitrobenzisothiazole (compounds 16, 11 and 1, Table).

P.3 7-Bromobenzisothiazole 100 ml of 3N hydrobromic acid are added to a suspension of 10 g of 7-aminobenzisothiazole in 30 ml of water. To the resulting suspension, cooled to 5° C., there is added dropwise a solution of 4.6 g of sodium nitrite in 10 ml of water, and the mixture is stirred for 3 hours at 0° C. The resulting solution is added dropwise to a solution at 50° C. of 12.4 g of copper(I) bromide in 230 ml of 3N hydrobromic acid. The product obtainable after water vapour distillation is purified by chromatography on silica gel with toluene:ethyl acetate 4:1 as eluant. The yield is 35% of the theoretical yield of 7-bromobenzisothiazole, compound no. 3 (Table).

P.4 7-Fluorobenzisothiazole

A solution of 1.14 g of sodium nitrite in 30 ml of water is added dropwise at 5° C. to a suspension of 2.5 g of 7-aminobenzisothiazole in 45 ml of water and 23 ml of concentrated hydrochloric acid. After stirring for 30 minutes at 5° C., the suspension is filtered, and 23 ml of a 40% solution of sodium tetrafluoroborate in water are immediately added to the filtrate. After one hour at 0° C., the crystals that have formed are filtered off and dried in air. Thermal decomposition of those crystals at from 140° to 160° C. followed by distillation yields 1.2 g of 7-fluorobenzisothiazole, compound no. 4 (Table).

P.5 7-Iodobenzisothiazole

A solution of 1.4 g of sodium nitrite in 50 ml of water is added dropwise at 5° C. to a suspension of 3.0 g of 7-aminobenzisothiazole in 30 ml of water and 67 ml of 1N hydrochloric acid, and the mixture is stirred for one hour at 0° C. That solution is added dropwise to a mixture of 10.6 g of potassium iodide, 150 ml of water and 150 ml of chloroform. After 30 minutes, the reaction mixture is rendered basic, and the organic phase is separated from the aqueous phase and dried. After purification by chromatography on silica gel with toluene:ethyl acetate 4:1, 1.1 g of 7-iodobenzisothiazole, compound no. 5 (Table), are isolated.

The following compounds can be prepared in accordance with the methods indicated:

TABLE

Compounds of formula I

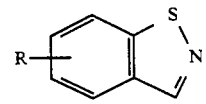

(I).

| Compound no. | R | Physical data |
| --- | --- | --- |
| 1 | 7-NO$_2$ | m.p.: 157-157.5° C. |
| 2 | 7-Cl | m.p.: 50-51° C. |
| 3 | 7-Br | m.p.: 58.5-60° C. |
| 4 | 7-F | $n_D^{20}$: 1.6612 |
| 5 | 7-I | m.p.: 70.5-71° C. |
| 6 | 6-NO$_2$ | |
| 7 | 6-Cl | $n_D^{20}$: 1.6424 |
| 8 | 6-Br | |
| 9 | 6-F | $n_D^{20}$: 1.6090 |
| 10 | 6-I | |
| 11 | 5-NO$_2$ | m.p.: 145-146° C. |
| 12 | 5-Cl | m.p.: 72-73° C. |
| 13 | 5-Br | resin |
| 14 | 5-F | $n_D^{20}$: 1.6059 |
| 15 | 5-I | |
| 16 | 4-NO$_2$ | m.p.: 109-115° C. |
| 17 | 4-Cl | m.p.: 41-43° C. |
| 18 | 4-Br | |
| 19 | 4-F | |
| 20 | 4-I | |

F. FORMULATION EXAMPLES FOR LIQUID ACTIVE INGREDIENTS OF FORMULA I (THROUGHOUT, PERCENTAGES ARE BY WEIGHT)

| F.1 Emulsifiable concentrates | a) | b) | c) |
| --- | --- | --- | --- |
| a compound of the Table | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | — | 12% |
| cyclohexanone | — | 15% | 20% |
| xylene mixture | 65% | 25% | 20% |

Emulsions of any desired concentration can be produced from such concentrates by dilution with water.

| F.2 Solutions | a) | b) | c) | d) |
|---|---|---|---|---|
| a compound of the Table | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| ligroin (boiling range 160–190° C.) | — | — | 94% | — |

These solutions are suitable for application in the form of micro-drops.

| F.3 Granules | a) | b) |
|---|---|---|
| a compound of the Table | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F.4 Dusts | a) | b) |
|---|---|---|
| a compound of the Table | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

FORMULATION EXAMPLES FOR SOLID ACTIVE INGREDIENTS OF FORMULA I (THROUGHOUT, PERCENTAGES ARE BY WEIGHT)

| F.5 Wettable powders | a) | b) | c) |
|---|---|---|---|
| a compound of the Table | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| F.6 Emulsifiable concentrate | |
|---|---|
| a compound of the Table | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required concentration can be obtained from this concentrate by dilution with water.

| F.7 Dusts | a) | b) |
|---|---|---|
| a compound of the Table | 5% | 8% |
| talcum | 95% | — |
| kaolin | — | 92% |

Ready-for-use dusts are obtained by mixing the active ingredient with the carrier and grinding the mixture in a suitable mill.

| F.8 Extruder granules | |
|---|---|
| a compound of the Table | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| F.9 Coated granules | |
|---|---|
| a compound of the Table | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| F.10 Suspension concentrate | |
|---|---|
| a compound of the Table | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

B. BIOLOGICAL EXAMPLES

B.1 Action against Meloidogyne incognita on tomato plants

Eggs of Meloidogyne incognita are mixed into sand. This mixture is then put into 200 ml clay pots (5000 eggs per pot). On the same day a three-week-old tomato plant is planted in each pot and the formulated test compound is introduced into the pots by drench application (0.0006% of active ingredient, based on the volume of the soil). The potted plants are then placed in a greenhouse at a temperature of 26°±1° C. and a relative humidity of 60%. After 4 weeks, evaluation is made by examining the plants for root-knot formation in accordance with the so-called Root-Knot Index.

The compounds of the Table exhibit activity against Meloidogyne incognita by reducing root-knot formation. On the other hand, untreated and infected control plants exhibit severe root-knot formation (=100%).

Compounds of formula I exhibit good activity with less than 20% residual attack, the compounds nos. 2 and 11, for example, even inhibit root-knot formation almost completely (0-10% residual attack) in this test.

B.2 Action against Heterodera glycines on soybeans

Sandy soil is infested with eggs of the soybean cyst nematode *H. glycines*, approximately 6000 eggs per pot. The test compounds are then mixed in at the appropriate concentrations. The treated and infested soil is then put into 1 c pots (180 ccm) and three soybeans (cv. Maple Arrow) are sown in each pot. Each treatment is repeated three times. The pots are incubated in a greenhouse at about 27° C. for four to five weeks. The plants are then carefully removed from the pots, the roots are washed, and the number of cysts is determined.

Compounds 1 and 2 of the Table exhibit good activity against *Heterodera glycines*, which is shown by the almost complete reduction of cyst formation.

What is claimed is:

1. A process for the preparation of a compound of formula I

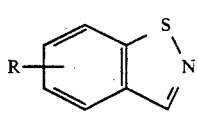  (I)

wherein R is nitro or halogen, which process comprises reacting a substituted halobenzaldehyde of formula V with a thioalcohol $R_9SH$ in solution, in the presence of a base, to form the thioether of formula VI, which is then reacted, with or without isolation, with hydroxylamine-O-sulfonic acid in solution and cyclised to form the desired product,

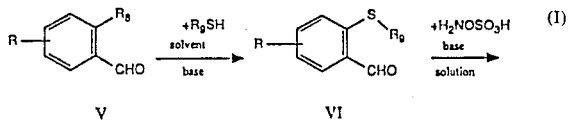  (I)

wherein R is nitro or halogen, $R_8$ is halogen and $R_9$ is $C_1$-$C_{30}$alkyl, $C_3$-$C_7$cycloalkyl or $C_7$-$C_9$aralkyl.

2. Process according to claim 1 wherein the thioether of formula VI is reacted with hydroxylamine-O-sulfonic acid in solution and cyclised by the addition of a base to form the desired product.

3. A process for the preparation of a compound of formula Ib

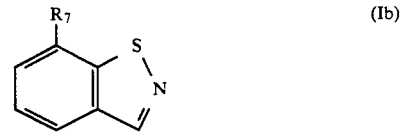  (Ib)

according to claim 18, which process comprises reacting a 2,3-dihalobenzaldehyde of formula VII with benzylmercaptan in solution, in the presence of a base, to form the thioether of formula VIII, which is then reacted, with or without isolation, with hydroxylamine-O-sulfonic acid in solution and cyclised to form the desired product,

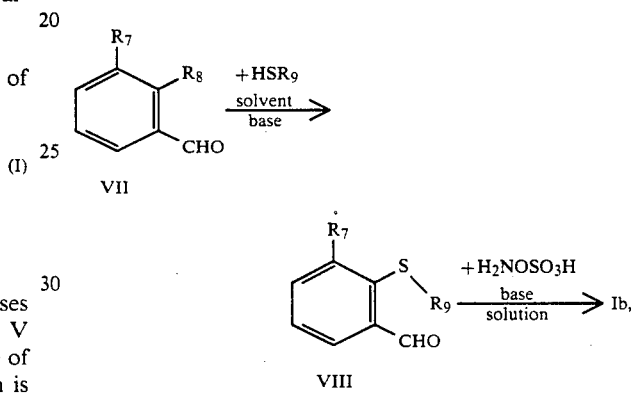

wherein $R_7$ and $R_8$ are identical or different halogens and $R_9$ is the benzyl radical.

4. Process according to claim 3, wherein the thioether of formula VIII is reacted with hydroxylamine-O-sulfonic acid in solution and cyclised by the addition of a base to form the desired product.

5. A process according to claim 4 wherein the intermediate of formula VIII is reacted with hydroxylamine-O-sulfonic acid at pH=5 and the cyclisation is effected by the subsequent addition of a base.

6. A process according to claim 3 wherein $R_7$ and $R_8$ are chlorine.

* * * * *